United States Patent [19]
Kroll et al.

[11] Patent Number: 5,833,712
[45] Date of Patent: Nov. 10, 1998

[54] IMPLANTABLE DEFIBRILLATOR SYSTEM FOR GENERATING A BIPHASIC WAVEFORM

[75] Inventors: Mark W. Kroll; Kai Kroll, both of Minnetonka, Minn.

[73] Assignee: Angeion Corporation, Plymouth, Minn.

[21] Appl. No.: 426,023

[22] Filed: Apr. 21, 1995

Related U.S. Application Data

[63] Continuation-in-part of Ser. No. 132,634, Oct. 6, 1993, abandoned, and a continuation-in-part of Ser. No. 292,354, Aug. 18, 1994, Pat. No. 5,507,781, which is a continuation of Ser. No. 999,393, Dec. 31, 1992, abandoned, which is a continuation-in-part of Ser. No. 704,619, May 23, 1991, Pat. No. 5,199,429.

[51] Int. Cl.$^6$ .................................................... A61N 1/39
[52] U.S. Cl. ..................................... 607/7; 607/5; 607/74
[58] Field of Search ........................................ 607/5, 7, 74

[56] References Cited

U.S. PATENT DOCUMENTS

| | | |
|---|---|---|
| 3,093,136 | 6/1963 | Lohr . |
| 3,241,555 | 3/1966 | Caywood et al. . |
| 3,886,950 | 6/1975 | Ukkestad et al. . |
| 3,924,641 | 12/1975 | Weiss . |
| 4,637,397 | 1/1987 | Jones et al. . |
| 4,638,397 | 1/1987 | Jones et al. . |
| 4,708,145 | 11/1987 | Tacker, Jr. et al. . |
| 4,800,883 | 1/1989 | Winstrom . |
| 4,830,006 | 5/1989 | Haluska et al. . |
| 4,850,337 | 7/1989 | Bach, Jr. . |
| 4,850,357 | 7/1989 | Bach . |
| 4,998,531 | 3/1991 | Bocchi et al. . |
| 5,083,562 | 1/1992 | de Coriolis et al. . |
| 5,163,427 | 11/1992 | Keimel . |
| 5,199,429 | 4/1993 | Kroll et al. . |
| 5,334,219 | 8/1994 | Kroll . |
| 5,360,435 | 11/1994 | DeGroot . |
| 5,395,395 | 3/1995 | Hedberg ...................................... 607/5 |
| 5,411,525 | 5/1995 | Swanson et al. . |
| 5,441,518 | 8/1995 | Adams et al. ................................ 607/5 |

FOREIGN PATENT DOCUMENTS

| | | | |
|---|---|---|---|
| 0272021 | 7/1964 | Australia ........................... 128/419 D |
| 0280526 | 8/1988 | European Pat. Off. . |

OTHER PUBLICATIONS

Kroll, MW et al., "Decline in Defibrillation Thresholds", PACE 1993, 16#1:213–217;.

Bardy, GH et al., "A prospective Randomized Evaluation of Biphasic vs. Monophasic Waveform Pulses on Defribrillation Efficiency in Humans", J. American College of Cardiology, 1989, 14:728–733;.

Wyse, DG et al., "Camparison of Biphasic and Monophasic Shocks for Defibrillation using a Non–Thoracotomy system" American J. Cardiology 1993; 71:197–202.

Fozzard HA, "Membrane Capacity of the Cardiac Purkinje Fiber," J. Physio (Great Britian) 1966; 182:255–267.

Weidmann S., "Electrical Constants of Trabecular Muscle from Mammalian Heart," J. Physio (Great Britian) 1970; 210:1041–1054.

(List continued on next page.)

*Primary Examiner*—William E. Kamm
*Assistant Examiner*—Kennedy J. Schaetzle
*Attorney, Agent, or Firm*—Brad Pedersen

[57] ABSTRACT

A method and apparatus for generating biphasic waveforms uses an implantable cardioverter defibrillator having two capacitor systems and a switching network. A first phase of the biphasic waveform is produced by configuring the two capacitor systems to selectively discharge first in a parallel combination, and then in a series combination. The second phase of the biphasic waveform is produced by reconfiguring the two capacitor systems in a parallel combination. By reverting to a parallel configuration for the second phase of the biphasic waveform, the output characteristics of the second phase of a biphasic waveform of the present invention more closely match a new model for understanding the effectiveness of the biphasic.

7 Claims, 6 Drawing Sheets

OTHER PUBLICATIONS

Knisley SB, Blitchington T.F., Hill, BC, "Optical Measurement of Ventricular Cells", Circulation Research 1993; 72:255–270.

Kroll, MW, et al., "A Minimal Model of the Monophase Defibrillator Pulse", PACE 1993; 16#4:769–777.

Freeser, et al. *Circulation,* vol. 82, No. 6, p. 2128, Dec. 1990.

Schuder, J.C. et al. Transthoracic Ventricular Defibrillation with Square–Wave Stimuli: One–Half Cycle, One Cycle and MultiCycle Waveforms, Circulation Research, 1964; 15:258–264.

Kavanagh, K.M. et al., Comparison of the Internal Defibrillation Thresholds for Monophasic and Double and Single Capacitor Biphasic Waveforms, J. American College of Cardiology, 1989; 14:1343–1349.

Freeser, S.A. et al., Strength–Duration and Probability of Success Curves for Defibrillation with Biphasic Waveforms, Circulation, 1990; 82:2128–2141.

Walker R.G., Walcott G.P., Swanson D.K. et al., Relationship of Charge Distribution between Phases in Biphasic Waveforms, Circulation 1992; 86 No. 4:I–792 (Abstract).

Gurvish H.L., Markarychev, V.A.: Defibrillation of the Heart with Biphasic Electrical Impulses, Kardiologilia 1967;7:109–112.

Tchou P., Krum D., Aktar M. Avitall B., Reduction of Defibrillation–Energy Requirements with new Biphasic Waveforms, PACE 1990; 13:507 (Abstract).

Jones J.L., Jones R.E., Balasky G., Improved Cardiac Cell Excitation with Symmetrical Biphasic Defibrillator Waveforms, American J. Physiology 1987; 253:H1418–H1424.

Kavanagh K.M., Duff H.J., Clark R., et al., Monophasic vs. Biphasic Cardiac Stimulation: Mechansim of Decreased Energy Requirements, PACE 1990:13; 1268–1276.

Swartz J.F., Jones J. L., Jones R.E., Fletcher R.D., Conditioning Prepulse of Biphasic Defibrillator Waveforms Enhances Refractoriness to Fibrillation Wavefronts, Circulation Research 1991;68:438–449.

Karasik P., Jones R., Jones J., Effect of Waveform Duration on Refractory Period Extension Produced by Monophasic and Biphasic Defibrillator Waveforms, PACE 1991; 14:715 (abstract).

Tang ASL, Yabe S., Wharton J.M. et al., Ventricular Defibrillation Using Biphasic Waveforms: The Importance of Phasic Defibrillation, J. American College of Cardiology 1989; 13:207–14.

Bourland J.D., Tacker W.A., Geddes L.A. et al., "Comparative Efficacy of Damped Sign Wave and Square Wave current for Transchest Ventricular Defibrillation in Animals", Medical Instrumentation 1978;12#1:38–41.

Irnich W., "The Chronaxie Time and its *Practical Improtance",* PACE 1980; 8:870–888.

Kroll M.W., Adams T.P., "The Optimum Pulse Width for the Implantable Defibrillator", 7th Purdue Conference on Defibrillation, American Heart Journal 1992; 124#3;835.

Schwartz J.F., Karasik P.E, Donofrio J. et al., "Effect of Biphasic Waveform Tilt on Human Non–Thoracotomy Defibrillation Treshold", PACE 1993;16#4II:888.

Ideker R.E., Tang A.S.L., Frazier D.W. et al., Ventricular Defibrillation: Basic Concepts:, Cardiac Pacing and Electrophysiology 3rd Ed., edited by El–Sherif N. & Samatt, W.B. Saunders Co. Philadelphia 1991;42:713–726.

Frazier D.W., Wolf P.D., Wharton J.M., et al., "A Stimulas Induced Critical Point: A Mechanism for Electrical Initiation of Re–Entry in Normal Canine Myocardium" J. of Clinical Investigation 1989;83:1039.

Shibata N., Chen P.S., DIxon E.G., et al., "Epicardial Activation After Unsuccessful Defibriallation Shocks in Dogs", American J. Physiology 1988;255:H902–H909.

Zhou X. Daubert J.P., Wolf P.D., et al., Epicardial Mapping of Ventricular Defibrillation with Monophasic and Biphasic Shocks in Dogs:, Circulation Research 1993;72:145–160.

Jones JL, Jones R.E., "Decreased Defibrillator–Induced Dysfunction with Biphasic Rectangular Waveforms", American J. Physiology 1984:247:H792–796.

Niebauer M.J., Babbbs C.F., Geddes L.A., et al., "Efficacy and Safety of the Reciprocal Pulse Defibrillator Current Waveform", Medical and Biological Engineering and Computing 1984;22:28–31.

Kavanagh, K.M. et al., Comparison of the Internal Defibrillation Thresholds for Monophasic and Double and Single Capacitor Biphasic Waveforms, J. American College of Cardiology, 1989; 14:1343–1349.

Feeser S.A., Tang A.S.L., Kavanagh K.M., et al., "Strength—Duration and Probability of Success Curves for Defibrillaion with Biphasic Waveforms" Circulation 1990;82:2128–2141.

Dixon E.F., et al., "Improved Defibrillaion Thresholds with Large Contoured Epicardial Electrodes and Biphasic Waveforms", Circulation, 1987;76:1176–1184.

Chapman , et al., "Efficacy of Monophasic and Biphasic Truncated Exponential Shocks for Nonthoracotomy Internal Defibrillation in Dogs", J. American College of Cardiology, 1988;12:739–745.

Dillon S.M., "Synchronized Depolarized after Defibrillation Shocks: A Possible Component of the Defibrillation Process Demonstrated by Optical Recordings in Rabbit Heart", Circulation 1992;85:1865–1878.

Sweeney R.J., et al., "Ventricular Refractory Period Extension Caused by Defibrillation Shocks", Circulation 1990;82:965–972.

Belz M.K. et al., "Successful Defibrillation Prolongs Action Potential Durations in Humans", PACE 993;16:932.

Frasier D.W. et al., Extracellular Field Required for Excitation in Three–Dimensional Anisotropic Canine Myocardium:, Circulation Research 1988;63:147–164.

Wessale J.L. et al., "Bipolar Catheter Defibrillation in Dogs using trapezoidal Waveforms of Various Tilts", J. Electrocardiology 1980;13(4):359–366.

Wharton J.M. et al., "Electrophysiological Effects in Vivo of Monophasic and Biphasic Stimuli in Normal and Infarcted Dogs", PACE 1990;13:1158–1172.

Niebauer M.J., Babbs C.F., Geddes L.A., et al., "Efficacy and Safety of Defibrillation with Rectangular Waves of 2 to 20–milliseconds Duration", Crit. Care Medicine 1983; 11#2:95–98.

Daubert J.P. et al., "Response of Relatively Refractory Canine Myocardium to Monophasic and Biphasic Shocks", Circulation 1991;84:2522–2538.

Zhou X. Daubert J.P., Wolf P.D., et al., "Prolongation of Repolorization Time by Electric Field Stimulation with Monophasic and Biphasic Shocks in Open Chest Dogs", Circulation Research 1991;68:1761–1767.

Yabe S., et al., "Conduction Disturbances Caused by High Current Density Electric Fields", Circulation Research 1990;66:1190–1203.

January C.T. et al., Early After Depolarization Newer Insights into Cellular Mechanisms;, J. Cardiovascular Electrophysiology 1990;1:161–169.

Shibata N. et al., "Epicardial Activation After Unsuccessful Defibrillation Shocks in Dogs", American J. Physiology 1988;255:H902–909.

Chen P.S. et al., "Epicardial Activation During Ventricular Defibrillation in Open–Chest Dogs", J. Clinical Investigation 1986;77:810–823.

Cooley J.W., Dodge F.A., "Digital Computer Solutions for Excitation and Propagation of the Nerve Impulse", Biophysical Journal 1966;6:583–599.

Krassowska W., et al., "Propagation vs Delayed Activation During Field Stimulation of Cardiac Muscle", PACE 1992;15:197–210.

Schwartzman D. et al., "Serial Patch — Patch Impedence Values in an Epicardial Defibrillation System", PACE 1993;16:916.

Cooper R. et al., "The Effect of Phase Separation on Biphasic Waveform Defibrillation", PACE, vol. 6, Mar., Part I, 1993.

Kao C.Y., Hoffman B.F., "Graded and Decremental Response in Heart Muscle Fiber", American J. Physiology 1958;194(1):187–196.

IMPLANTABLE DEFIBRILLATOR SYSTEM FOR GENERATING A BIPHASIC WAVEFORM

RELATED APPLICATIONS

This application is a continuation-in-part application of two patent applications filed in the United States Patent and Trademark Office, the first of which is entitled "METHOD AND APPARATUS FOR GENERATING BIPHASIC WAVEFORMS IN AN IMPLANTABLE DEFIBRILLATOR", Ser. No. 08/132,634, filed Oct. 6, 1993, now abandoned, and the second of which is entitled "IMPLANTABLE DEFIBRILLATOR SYSTEM", Ser. No. 08/292,354, filed Aug. 18, 1994, and now issued as U.S. Pat. No. 5,507,781, which is a continuation of Ser. No. 07/999,393, filed Dec. 31, 1992, now abandoned, which is a continuation-in-part of an application entitled "IMPLANTABLE DEFIBRILLATOR SYSTEM EMPLOYING CAPACITOR SWITCHING NETWORKS", Ser. No. 07/704,619, filed May 23, 1991, and now issued as U.S. Pat. No. 5,199,429, both of which are assigned the same assignee as the present invention, the disclosure of each of which is incorporated by reference and a copy of each of which is attached hereto.

FIELD OF THE INVENTION

The present invention relates generally to implantable defibrillator systems, and more particularly, to a method and apparatus for generating biphasic waveforms with an implantable defibrillator system.

BACKGROUND OF THE INVENTION

Implantable defibrillator systems deliver a high voltage electrical countershock to the heart in an attempt to correct or convert a detected cardiac arrhythmia or fibrillation. Due to the limitations on size and power imposed by the fact that these systems must be self-contained implantable devices, all existing implantable defibrillator systems generate an electrical countershock by charging a capacitor system to a high voltage from a low voltage battery and oscillator circuit. The battery is then switched out of the circuit and the electrical charge stored in the capacitor system is delivered as a truncated capacitive discharge through two or more implanted electrodes.

To date, there have been two basic kinds of discharge waveforms which have been used with implantable defibrillator systems: monophasic waveforms and biphasic waveforms; both of which are delivered as a truncated capacitive discharge. Monophasic waveforms are comprised of a single monotonically decaying electrical pulse that is typically truncated before the capacitor system is completely discharged. Biphasic waveforms, on the other hand, are comprised of a decaying electrical pulse that has a pair of decaying electrical phases that are of opposite polarity. To generate a biphasic pulse an H-bridge switch circuit connected to the electrodes is used to switch the polarity of the two phases. In generating the biphasic pulse, a first phase is discharged from the capacitor system, much in the same manner as a monophasic pulse. At the point in time that the first pulse is truncated, the H-bridge switch circuit immediately reverses the discharge polarity of the capacitor system as seen by the electrodes to produce the second phase of the biphasic waveform that is of the opposite polarity. A typical example of the use of an H-bridge circuit to generate a biphasic waveform in an implantable defibrillator system is shown in U.S. Pat. No. 4,998,531.

Over the last twenty five years, it has been demonstrated that appropriately truncated biphasic waveforms can achieve defibrillation with significantly lower currents, voltages and energies than monophasic waveforms of similar durations. Kroll, MW et al., "Decline in Defibrillation Thresholds", *PACE* 1993; 16#1:213–217; Bardy, GH et al., "A Prospective Randomized Evaluation of Biphasic vs. Monophasic Waveform Pulses on Defibrillation Efficiency in Humans", *J American College of Cardiology*, 1989; 14:728–733; and Wyse, DG et al., "Comparison of Biphasic and Monophasic Shocks for Defibrillation using a Non-Thoracotomy System", *American J Cardiology* 1993; 71:197–202. These findings are of particular importance for implantable devices because of the direct relationship between the amount of energy required for defibrillation and the overall size of the implantable device, i.e., the lower the energy required for defibrillation, the smaller the device.

Numerous theories have been advanced to explain the improved efficiency of the biphasic waveform over the more conventional monophasic waveform. Although some of these theories may partly explain, or may act cooperatively to explain, the effect a biphasic waveform has on the heart, there is currently no single accepted theory which fully explains the advantages of the biphasic waveform over the monophasic waveform. As a result, there is little or no agreement on what factors might further improve the efficiency and operation of the biphasic waveform.

In the previously identified parent application entitled "IMPLANTABLE DEFIBRILLATOR SYSTEM EMPLOYING CAPACITOR SWITCHING NETWORKS", a system for delivering a novel biphasic waveform is described in which two capacitor systems are used to store the electrical charge for the electrical countershock. To generate this biphasic waveform, the capacitor systems are configured in parallel for delivering a first phase of the biphasic waveform and in series for delivering a second phase of the biphasic waveform.

In the other previously identified parent application entitled "METHOD AND APPARATUS FOR GENERATING BIPHASIC WAVEFORMS IN AN IMPLANTABLE DEFIBRILLATOR", a new model is presented for understanding why the biphasic waveform is more effective than a monophasic waveform. Applying this new model, another system for delivering a novel biphasic waveform is described in which two capacitor systems are used to store the electrical charge for the electrical countershock. A first phase of the biphasic waveform for this system is delivered from a first electrical charge stored in a first capacitor system, and a second phase of the biphasic waveform is delivered from a second electrical charge stored in a second capacitor system. To maximize the effectiveness of the biphasic waveform according to the new model, this system teaches that the second electrical charge should be of less energy and should be stored separate and distinct from the first electrical charge.

SUMMARY OF THE INVENTION

The present invention provides a method and apparatus for generating biphasic waveforms uses an implantable cardioverter defibrillator having two capacitor systems and a switching network. A first phase of the biphasic waveform is produced by configuring the two capacitor systems to selectively discharge first in a parallel combination, and then in a series combination. The second phase of the biphasic waveform is produced by reconfiguring the two capacitor systems in a parallel combination. By reverting to a parallel configuration for the second phase of the biphasic waveform, the output characteristics of the second phase of a biphasic waveform of the present invention more closely match the new model for understanding the effectiveness of the biphasic waveform.

Many theories have been offered for the improved efficacy of the biphasic defibrillation waveform. The present invention is derived from the use of a unique quantitative model based on the theory that the function of the first phase of the biphasic waveform is to synchronize the heart cells in the same manner as a conventional monophasic wave, and the function of the second phase is to remove any residual charge from the cell membranes that may have been deposited by the first phase of the countershock. The model used by the present invention assumes that the effective current requirement of the first phase is a linear function of the calculated residual (after the second phase) cell membrane voltage squared. The present invention uses this model to optimize the generation of biphasic waveforms for an implantable defibrillator having a first stage capacitance discharge by a combination of a parallel and series configuration of at least two capacitor systems and a second stage capacitance discharge by reverting to a parallel configuration of the at least two capacitor systems.

In accordance with a first aspect of the present invention, an implantable cardioverter defibrillator apparatus discharges a mode reversal biphasic electrical countershock to an ailing human heart through at least two implantable electrodes located proximate the heart. The apparatus comprises an internal power source for providing electrical energy and a capacitance system electrically connected between the power source and the electrodes. The capacitance system stores electrical energy to generate a first phase and a second phase of the biphasic countershock. The capacitance system includes at least two capacitor units each having separably switchable cathodes and anodes. A control system, operatively coupled to the power source and the capacitance system, controls delivery of the first phase and second phase of the biphasic countershock from the capacitance system to the electrodes in response to a sensing of a cardiac dysrhythmia. The control system determines the topology and polarity of the at least two capacitor units such that the first phase has a first polarity across the electrodes and the at least two capacitor units are configured first in a parallel configuration and then in a series configuration during the first phase, and the second phase has a second polarity across the electrodes and the at least two capacitor units are configured in a parallel configuration during the second phase.

In accordance with a second aspect of the present invention, a method is described for operating an implantable cardioverter defibrillator device implanted within a human patient and electrically connected to at least two implantable electrodes located proximate a human heart to treat a cardiac arrhythmia by delivering a mode reversal biphasic electrical countershock. The method comprises the device-implemented steps of: (a) sensing for a cardiac dysrhythmia in a human patient and, in response, performing the steps of (b1) charging a capacitive charge storage system to a high voltage charge value using a low voltage power source, the capacitive charge storage system including at least two capacitor units each having separably switchable cathodes and anodes; (b2) discharging at least a first portion of the charge value stored in the capacitive charge storage system through the electrodes with the at least two capacitor units configured first in parallel and then in series to produce the first phase of the biphasic countershock; and (b3) discharging at least a second portion of the charge value stored in the capacitive charge storage system through the electrodes with the at least two capacitor units configured in parallel to produce the second phase of the biphasic countershock having an opposite polarity from the first phase.

DETAILED DESCRIPTION OF THE INVENTION

Figure 1:
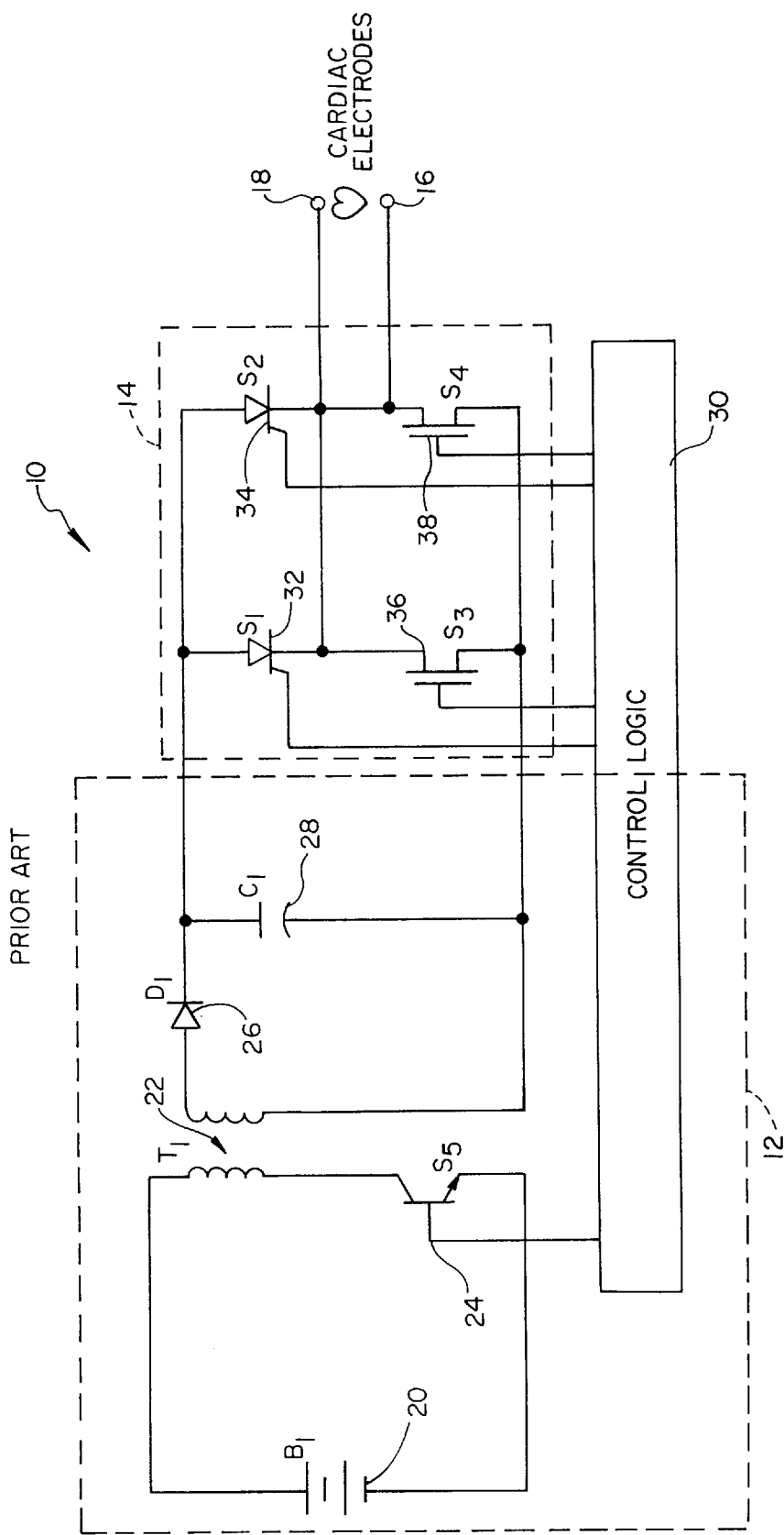
FIG. 1 is a schematic diagram of an ICD of the prior art.

In FIG. 1, a prior art example of an implantable cardioverter defibrillator (ICD) is depicted by circuitry 10 which includes a high output voltage circuit 12 selectively connected through an H-bridge switch 14 to cardiac electrodes 16, 18. High voltage circuit 12 is comprised of a battery power source 20, a secondary fly back transformer 22, transistor switch 24 and rectifying diode 26 that enable battery power source 20 to store a high voltage electrical charge in a high voltage storage capacitor system 28 under control circuit logic 30. H-bridge 14 includes switch 32, switch 34, switch 36, and switch 38.

Figure 2:
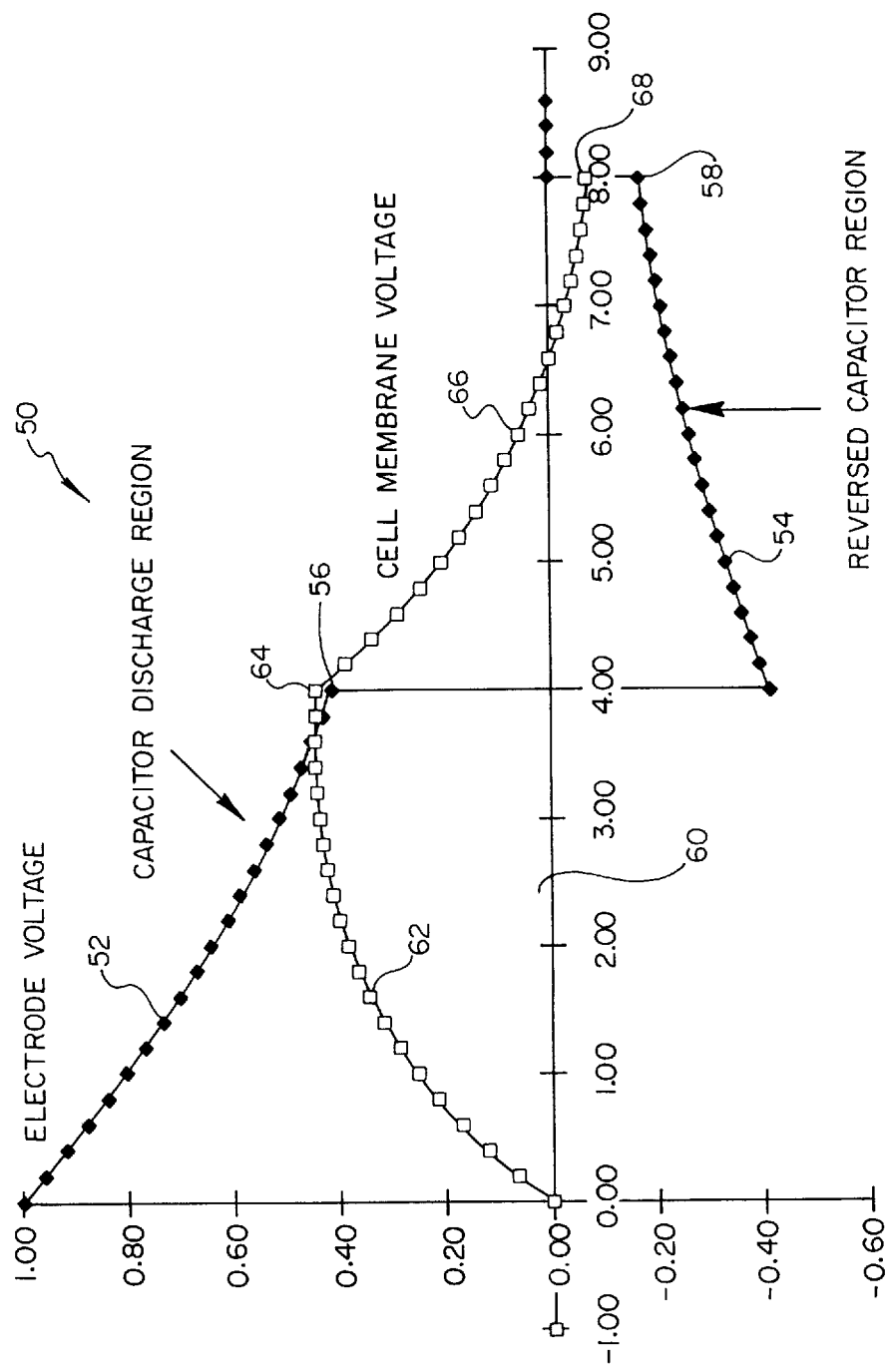
FIG. 2 depicts a representative voltage output for a biphasic waveform as generated by the ICD of FIG. 1.

A representative voltage output of the ICD circuit depicted in FIG. 1 is shown in FIG. 2. As shown in FIG. 2, output curve 50 has a positive first phase 52 and a negative second phase 54 with phase transition occurring at curve 56 and truncation of output at curve 58. A cell membrane voltage curve 60 is also shown in FIG. 2 depicting the cell membrane voltage response to the ICD output voltage shown in curve 50. A first phase curve 62 rises to transition 64 which corresponds to phase transition curve 56 at which time cell membrane voltage curve 60 enters a second phase 66 illustrating a decaying voltage to discharge truncation at 68.

It will be noted in FIG. 2 that output curve 50 decays from a normalized maximum voltage of 1.0 to about 0.42 of that voltage at about 4 ms at transition 56. The cell membrane voltage 60 is determined by theoretical calculations of the resulting cell membrane voltage in the heart cells when subjected to output curve 50. Cell membrane time constants for human heart cells are well documented in the medical research literature ranging from 1–6 ms, with 3 ms being the norm for most study results, so it is calculation that the heart cells have an intrinsic time constant of about 3 ms. At transition 64, the cell membrane voltage has peaked at about 0.45 of its normalized maximum. During the second phase 54 of output curve 50, the second phase 66 of the cell membrane voltage discharges fairly rapidly and is restored to a zero voltage at about 6.5 ms.

For the reasons discussed in greater detail hereinafter, output curve 50 does not make optimal use of the electrical charge stored in capacitors 24, 26 for two reasons. First, the positive phase duration is about 4 ms, as opposed to the theoretical optimal duration of the first phase which should be on the order of 2.4–3.0 ms, the "chronaxie" time for the human heart cell. Second, cell membrane voltage 60 is restored to zero volts by second phase 66, but is then "pulled through" zero volts such that the cell membrane is left with a negative voltage value at the truncation 58 of output curve 50. The new theoretical model which is disclosed in the present invention suggests that the cell membrane voltage should be left at a voltage value very near zero at the end of a defibrillation countershock in order to prevent refibrillation. By doing so, it turns out that the amplitude requirements for the first phase of a biphasic countershock are effectively lowered. By not leaving the cell membrane voltage at a zero potential at the end of an electrical countershock, it is necessary that the electrical energy imparted to the heart cells by the first phase of the countershock must be greater so as to prevent any refibrillation caused by the residual voltage on the cell membranes left at the end of the countershock.

Figure 3:
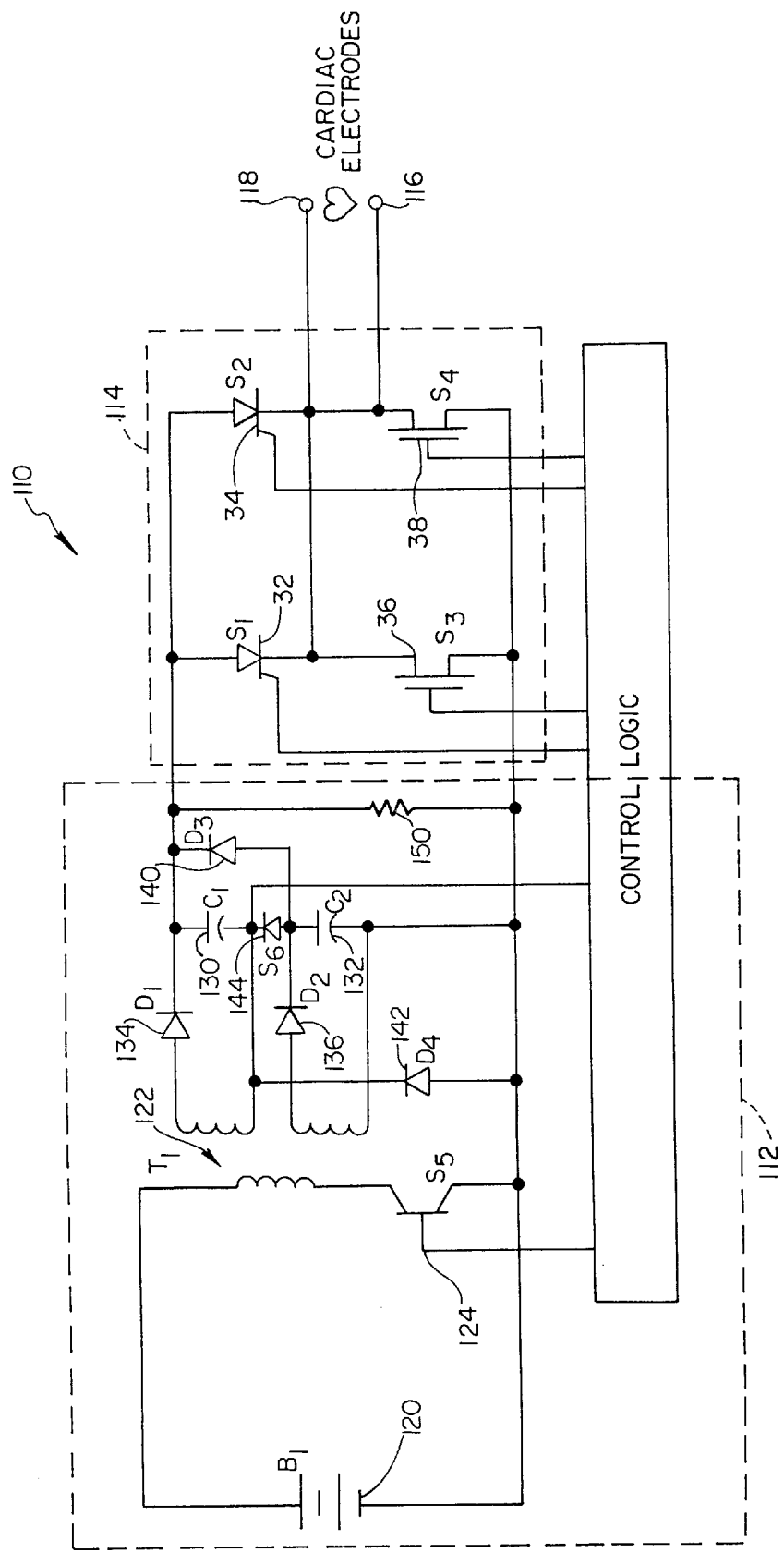
FIG. 3 is a schematic diagram of an ICD in accordance with the present invention.

Turning to FIG. 3 there is depicted an ICD 110 in accordance with the present invention comprising a high voltage output circuit 112, H-bridge switch 114 and cardiac electrodes 116, 118. As with ICD 10 in the prior art, high output voltage circuit 112 includes a battery source 120, a flyback split winding transformer 122, and an oscillating transistor switch 124. Unlike ICD 10 in the prior art, ICD 110 includes at least two separate high voltage capacitor systems 130 and 132 coupled to transformer 122 by rectifying diodes 134 and 136. Diodes 140 and 142 and SCR switch 144 provide a switching network under selective control of controller 108 that allows an output 150 across H-bridge switch 112 to be selectively configured as either a parallel or series combination of capacitor systems 130 and 132. Controller 108 is preferably a microprocessor or microcontroller operating under software control, however, it will be recognized that controller 108 could also be implemented as discrete or integrated logic circuits. In acceleration it would also be possible to use, for example, a four way split transformer.

It should be noted that capacitor systems 130 and 132 are not merely a single capacitor system but implemented using, for example, two photoflash capacitors configured in series, each capable of storing up to a 375 V charge with a midpoint tap in transformer 22 and two rectifying diodes each used to charge one of the two photoflash capacitors, respectively, that together comprise capacitor 28 of ICD 10. Each capacitor system 130 and 132 is a capacitor arrangement that has separate accessible cathode and anode outputs that are independently switchable under control of controller 108. For example, each of capacitor systems 130 and 132 could be implemented as a pair of photoflash capacitors in series, for a total of four photoflash capacitors used in high voltage circuit 112. Alternatively, capacitor systems 130 or 132 could each be implemented as a single high voltage film capacitor or even as a combination of double layer capacitors.

Figure 4:
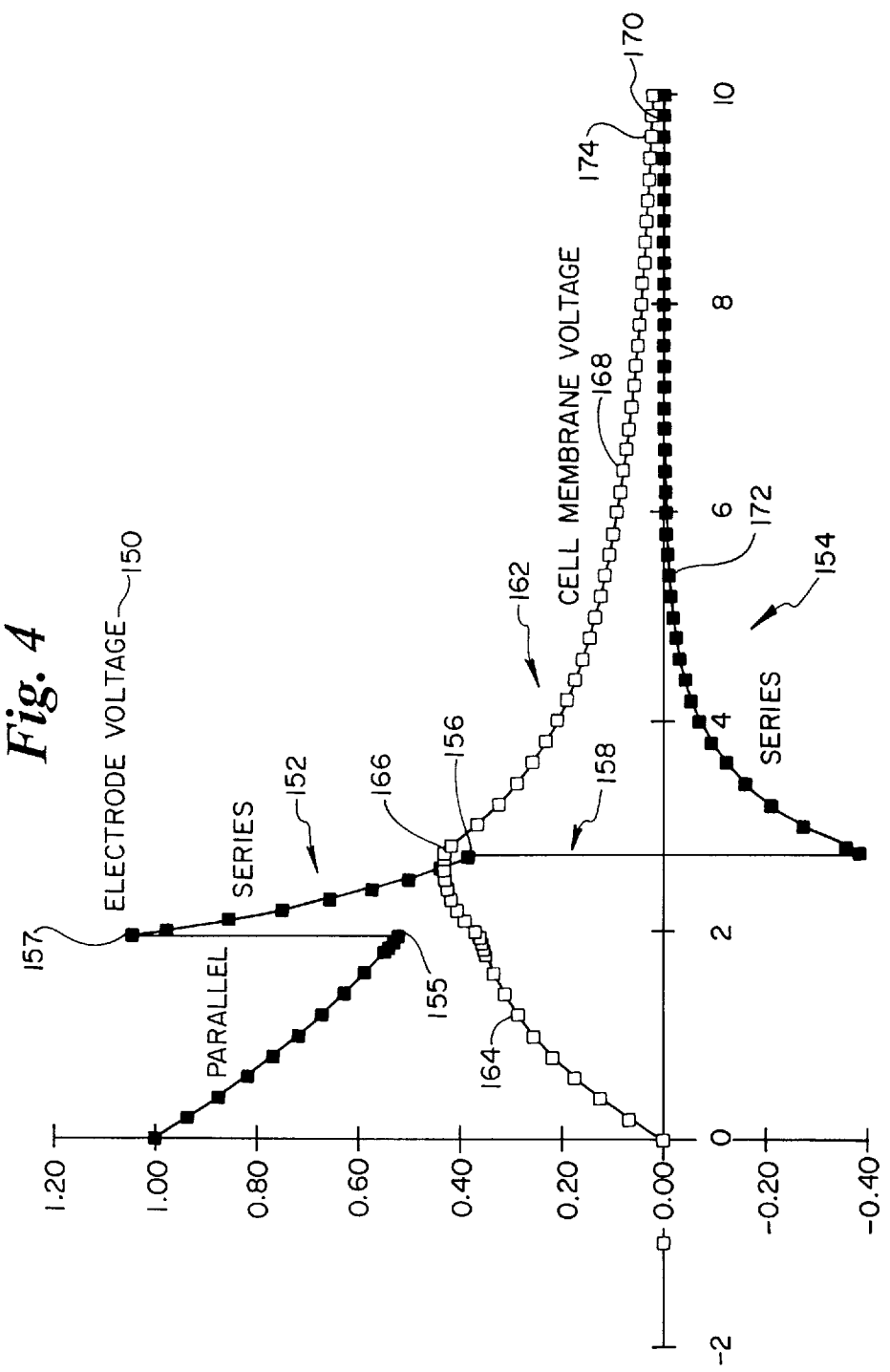
FIG. 4 depicts a representative voltage output for a biphasic waveform as generated in accordance with the parent application to the present invention.

FIG. 4 discloses a representative output for an ICD of the previously identified co-pending application entitled "METHOD AND APPARATUS FOR GENERATING BIPHASIC WAVEFORMS IN AN IMPLANTABLE DEFIBRILLATOR". As shown in FIG. 4, voltage output is characterized by curve 150 which includes a positive first phase 152 and a negative second phase 154 separated by a transition period 158 with the entire biphasic waveform output ending at truncation 160. At the start of first phase 152, switch 144 (as shown in FIG. 3) is not enabled and capacitor systems 130 and 132 are configured in parallel so as to provide a normalized output voltage of 1.0 that decays to about 0.5 at about 2 ms. At this point 155, capacitors 130, 132, are switched into a series configuration by enabling switch 144 so as to effectively double the voltage output at point 157 to slightly over 1.0 of the normalized maximum voltage. The series configuration is maintained for approximately 0.8 ms, at which point first phase 152 is truncated at point 156. The preferred durations of the parallel and series portions of first phase 152 are determined based on an optimization analysis as set forth below, however, it will be recognized that different durations of each portion may be used. Alternatively, more than two capacitor units 130, 132 may be used, in which case multiple combinations of parallel and series topology for the three or more capacitor units would be possible. During second phase 154, capacitors 130, 132 remain in a series configuration until truncation point 160.

Also depicted in FIG. 4 is cell membrane voltage curve 162 illustrating the cell membrane voltage response to the output of an ICD of the present invention. Cell membrane curve 162 includes a positive phase rising voltage curve 164 that reverses its rise at 166 which corresponds to high voltage truncation 156 on curve 150. During the negative phase 154 cell membrane curve 168 decreases to 170 which corresponds to truncation 160 when the discharge of the second phase is completed.

New Model For Biphasic Waveforms

A discussion of various theories and experimental results related to biphasic waveforms is set forth in the previously identified co-pending application entitled "METHOD AND APPARATUS FOR GENERATING BIPHASIC WAVEFORMS IN AN IMPLANTABLE DEFIBRILLATOR". While many models and experiments have been performed on the biphasic waveform, other than the model set forth in the co-pending application there are no clear explanations for why the biphasic waveform is more efficient that the monophasic waveform. Consequently, there is no clear guidance on how, or even if, improvements can be made to the generation and delivery of biphasic waveforms. The present invention use the model for the biphasic waveform set forth in the co-pending application to explain why an active energy second phase delivery of a biphasic waveform in accordance with the present invention is more efficacious than the existing technique of delivering biphasic waveforms from a single capacitor system.

The model that is utilized by the present invention is that the second phase of the biphasic waveform (when optimally sized) serves to remove the excess charge remaining on the cell membrane from the first phase. It is hypothesized that the excess charge remaining on cells after the countershock stimulation may end up creating a new arrhythmia some time after the countershock stimulation. Consequently, for a monophasic shock to be successful, it must not only capture enough cells to halt fibrillation, but it must also capture enough cells so that no post shock arrhythmias will occur as a result of the excess charge remaining on the cell membrane. In other words, by having the second phase of a biphasic countershock return the cell membrane potentials to their pre-shock potential, there are fewer post shock arrhythmias, and, because there are fewer post shock arrhythmias, fewer cells need to be synchronized by the first phase. In addition, the protective refractory period extension requirement may be reduced. It is theorized that these two factors may explain the reduced amplitude requirements for the first phase.

The circuit model of the cell that is implicit in this discussion is essentially the standard capacitive membrane coupled to resistive paths giving a membrane time constant. Fozzard HA, "Membrane Capacity of the Cardiac Purkinje Fiber", *J Physiol* (*Great Britain*) 1966;182:255–267. In this model, $V_e$ represents the voltage across the defibrillation electrodes and $V_m$ represents the voltage across the membrane. The exact values of the resistances and capacitance are not important, the salient feature is the resulting membrane time constant which will be called $\tau_m$.

Referring again to FIG. 2, the voltages are shown as a function of time which would be expected in such a model for a biphasic waveform delivered from an existing ICD system having a single capacitor system. Assuming an ICD capacitance of 150 μF and an electrode resistance of 50 Ω, the electrode voltages will be as shown for a biphasic wave, with each phase having a duration of 3.5 ms. For ease of notation, the remaining discussion will refer to the duration of the a biphasic waveform in a shorthand form as "3.5/3.5", indicating that the first phase is 3.5 ms and the second phase is 3.5 ms. The capacitor voltages 51 and 53 for the first and second phases of the waveform 50 are shown beginning at a normalized value of 1.00 volts. The membrane voltages 60 are calculated with the use of a representative time constant of the non-Purkinje ventricular cell membrane of approximately 3 ms. Weidmann S, "Electrical Constants of Trabecular Muscle from Mammalian Heart", *J Physiol* (*Great Britain*) 1970;210: 1041–1054.

The exact transmembrane potential of an individual cell is not relevant for this analysis. What is important is the perturbation, by the first phase 52 of the defibrillation countershock, of the membrane voltage 60 from its existing value. The model of the biphasic waveform utilized by the present invention suggests that the cancellation of this perturbation, i.e. the "burping" of the membrane charge, appears to be the critical function of the second phase. As can be seen from FIG. 2, at the end of the second phase, the transmembrane potential has been left, in this case, with a negative perturbation potential 63 as a result of the delivery of the biphasic waveform, instead of the desired zero perturbation potential which is the goal of the theory of the present invention.

The membrane voltage $V_m$ is calculated as a fraction of the maximum potential attainable for an infinitely long rectangular pulse at the electrodes. The absolute value of the potential (in volts) is not critical as the return to zero is the sole goal of the biphasic waveform in accordance with the theory of the present invention. During the defibrillation shock the electric field will charge areas of the cell membrane positively, some negatively, and some not at all. Knisley SB, Blitchington TF, Hill BC, "Optical Measurement of Transmembrane Potential Changes During Electric Field Stimulation of Ventricular Cells", *Circulation Research* 1993;72:255–270. Also, depending upon the location of the cells vis-a-vis the electrodes, the actual membrane voltage will vary significantly. Using a normalized value (i.e. a fraction) for $V_m$ allows the model to concentrate on the simple goal of returning the membrane voltage to a zero perturbation.

A quantitative model for the present invention can be determined using a model for discussing the effects of a countershock on the myocardium. The myocardium has resistance and capacitance characteristics, but the exact values of the resistances and capacitance are not important. The relative contribution to the time constant of the series resistances and the shunt resistances (from the so called leaky-capacitor model) is also not important. The salient feature is the resulting myocardial cell membrane time constant which will be called $\tau_m$. $V_e$ represents the voltage across defibrillation electrodes, and $V_m$ represents the voltage across the cell membrane.

The analysis begins by temporarily ignoring the circuitry of the ICD and eliminating the resistance in parallel with the membrane capacitance in favor of simplicity. This parallel (leaky membrane) resistance may be ignored if $R_m$ is taken as the Thevenin equivalent of two resistors. Thus, $R_m$ and $C_m$ are the membrane series resistance and capacitance respectively. As before, the node $V_e$ represents the voltage between the electrodes, while $V_m$ denotes the voltage across the cell membrane. Nodal analysis provides an equation for the solution of $V_m$:

$$C_m \frac{dV_m}{dt} + \frac{V_m - V_e}{R_m} = 0. \tag{1}$$

Rearranging equation 1 to solve for $V_e$, we have $$V_e = V_m + (R_m C_m) \frac{dV_m}{dt}. \tag{2}$$

The discharge of a single capacitor in such a circuit is well-known and modeled by $$V_e = e^{(-t/R_s C_s)}$$

and so may be placed into equation 2 to give:

$$\tau_m \frac{dV_m}{dt} + V_m = e^{(-t/\tau_s)}, \tag{3}$$

where $\tau_m = R_m C_m$ represents the time constant of the myocardial cell in the circuit model, and $\tau_s = R_s C_s$ represents the time constant of the defibrillator shock in the circuit model. This differential equation models the effects of a monophasic, time-truncated, capacitor-discharge defibrillator on the myocardium.

Equation 3 is a first-order linear differential equation, and may be written as $$\frac{dV_m}{dt} + \left(\frac{1}{\tau_m}\right) V_m = \left(\frac{1}{\tau_m}\right) e^{(-t/\tau_s)}. \tag{4}$$

In the form of equation 4, the general solution is $$V_m = e^{-t/\tau_m} \left( \int \left( e^{t/\tau_m} \left(\frac{1}{\tau_m}\right) e^{-t/\tau_s} \right) dt + c \right). \tag{5}$$

where c is an integration constant. Integrating equation 5 and simplifying the resultant expression, we have for the membrane voltage at the end of the first phase:

$$V_{m_1}(t) = c e^{-t/\tau_m} + \frac{\tau_s}{\tau_s - \tau_m} e^{-t/\tau_s}. \tag{6}$$

To determine the constant of integration c, we assume the initial value for $V_m$ to be $V_{m1}(0)=0$. Applying the initial condition to equation 6, we have $$c = -\frac{\tau_s}{\tau_s - \tau_m}.$$

Therefore, the solution to our initial-value problem for phase 1 is $$V_{m_1}(t) = \frac{\tau_s}{\tau_s - \tau_m} (e^{-t/\tau_s} - e^{-t/\tau_m}). \tag{7}$$

A biphasic waveform reverses the flow of current through the myocardium during the second phase. A simplified model of the myocardial cell may again be used by merely reversing the flow of current in the circuit model by changing the sign on the shock current. We thus derive an almost identical differential equation to equation 3 above. The difference is the sign on the right hand side:

$$\tau_m \frac{dV_m}{dt} + V_m = -e^{(-t/\tau_s)}. \tag{8}$$

At the beginning of phase 1, we assumed a normalized value of 1 for the charge found on the capacitor at the time the defibrillation shock was initiated, so that equation 3 may be more explicitly written as $$\tau_m \frac{dV_m}{dt} + V_m = 1 \cdot e^{-t/\tau_s}.$$

At the beginning of phase 2, the capacitor has discharged for a period of time equal to the length of phase 1, and we shall denote this time period as $d_1$ (the duration of phase 1). The normalized capacitor charge at the start of phase 2 is therefore $e^{-d_1/\tau d} < 1$, and so equation 8 may be written more explicitly as $$\tau_m \frac{dV_m}{dt} + V_m = -e^{-d_1/\tau_s} \cdot e^{-t/\tau_s}. \tag{9}$$

Equation 9 is again a first-order linear differential equation, and we write this equation in the form below to apply standard methods for determining its solution:

$$\frac{dV_m}{dt} + \left(\frac{1}{\tau_m}\right) V_m = -\left(\frac{1}{\tau_m}\right) \cdot e^{-d_1/\tau_s} \cdot e^{-t/\tau_s}. \tag{10}$$

In the form of equation 10, the general solution is $$V_{m_2}(t) = c e^{-t/\tau_m} - \frac{\tau_s}{\tau_s - \tau_m} \cdot e^{-d_1/\tau_s} \cdot e^{-t/\tau_s}. \tag{11}$$

To determine the constant of integration c, we note that at the end of phase 1 the (initial) value for $V_{m_2}$ is $$V_{m_2}(0) = V_{m_1}(d_1) = \frac{\tau_s}{\tau_s - \tau_m} (e^{-d_1/\tau_s} - e^{-d_1/\tau_m}).$$

Applying the initial condition to equation 11, we have $$c = \frac{\tau_s}{\tau_s - \tau_m} K_m,$$

where $$K_m = 2e^{-d_1/\tau_s} - e^{-d_1/\tau_m}.$$

Therefore, the solution to the initial-value problem for phase 2 is $$V_{m_2}(t) = -\frac{\tau_s}{\tau_s - \tau_m} (K_s e^{-t/\tau_s} - K_m e^{-t/\tau_m}), \tag{12}$$

where $$K_s = e^{-d_1/\tau_s}.$$

which may be rewritten as:

$$V_{m_2} = \left[\frac{\tau_s}{\tau_s - \tau_m}\right] [(2e^{-d_1/\tau_s} - e^{-d_1/\tau_m})e^{-d_2/\tau_m} - e^{-d_1/\tau_s}e^{-d_2/\tau_s}] \tag{13}$$

The requirement defining an optimal pulse duration for phase 2 is that the phase 2 pulse leave as little residual membrane potential remaining on a non-depolarized cell as possible. Equation 12 provides a means to calculate the residual membrane potential at the end of the second phase for those cells that did not depolarize. To determine the optimal phase 2 pulse duration, we set equation 12 equal to zero and solve for t. This optimal pulse duration for phase 2, then, is $d_2$. To begin, we have $$0 = -\frac{\tau_s}{\tau_s - \tau_m} (K_s e^{-t/\tau_s} - K_m e^{-t/\tau_m}).$$

Because $(\tau_s/(\tau_s - \tau_m))$ cannot be zero, we solve for t using the equation $$0 = K_m e^{-t/\tau_m} - K_s e^{t/\tau_s}.$$

Arranging the exponential functions onto the left hand side, we get $$\frac{e^{-t/\tau_s}}{e^{-t/\tau_m}} = \frac{K_m}{K_s}. \tag{14}$$

Taking the logarithm of each side, solving for t, and rearranging terms, we get $$t = \left(\frac{\tau_s \tau_m}{\tau_s - \tau_m}\right) \cdot \ln\left(\frac{K_m}{K_s}\right) \tag{15}$$

and $$d_2 = \left[\frac{\tau_s \tau_m}{\tau_s - \tau_m}\right] \cdot \ln\left\{2 - \left[\frac{e^{-d_1/\tau_m}}{e^{-d_1/\tau_s}}\right]\right\}. \tag{16}$$

For typical values of a 140 μF capacitor and a 50 Ω electrode resistance the time constant ($\tau_s$) will be 7 ms. Assume that $\tau_m$ is the membrane time constant. The durations of the two phases will be referred to as $d_1$ and $d_2$ respectively. The membrane potential at the end of phase one will be given by Equation 7 as $$V_{m1} = (\tau_s/(\tau_s - \tau_m))[(e^{-d_1/\tau_s} - e^{-d_1/\tau_m}) \tag{17}$$

The subtraction of the two exponentials represents the attempt by the discharge capacitor of the ICD (as represented by the positive term with time constant $\tau_s$) to charge the membrane while the membrane capacitance is resisting the charging with its electrical inertia (as represented by the negative term containing $\tau_m$).

The membrane voltage at the end of the second phase is given as the following equation rearranged from Equation 12:

$$V_{m2} = (\tau_s/(\tau_s - \tau_m))[(2e^{-d_1/\tau_s} - e^{-d_1/\tau_m}) e^{-d_2/\tau_m} e^{-d_1/\tau_s} e^{-d_2/\tau}] \tag{18}$$

This intimidating equation is necessary to reflect the interaction between the two phase durations and two the time constants.

The fundamental hypothesis of the model of the present invention is that a low residual membrane voltage lowers the electrical requirements of the first phase. The lower residual membrane voltage, as a result of the second phase of the shock, reduces the necessary current of phase one that would otherwise be required to extinguish the additional local arrhythmias caused by the higher residual membrane voltage.

The electrical content of the first phase could be represented in many fashions. To correct for varied durations, the "effective" current model is used as set forth in Kroll, MW, et al., "A Minimal Model of the Monophase Defibrillator Pulse", *PACE* 1993; 16#4:769–777. The effective current is simply the average current divided by the "duration correction" such that the effective current of a defibrillation countershock (either monophasic or the first phase of a biphasic countershock) is simply the delivered charge divided by the sum of the chronaxie time and the pulse duration:

$$I_e = Q_{del}/(d_c/d) \tag{19}$$

The effective current is also equal to the rheobase current for shocks exactly at the threshold level. The function of the duration correction is to normalize the average current for the higher requirements of narrower pulses which is given by the strength duration curve. The duration correction is:

$$1 + (d_c/d) \tag{20}$$

and thus the effective current is given by:

$$I_{eff} = I_{ave}[1 + (d_c/d)] \tag{21}$$

The model of the present invention predicts that the required effective current has a minimum value which will be referred to as $I_o$ for a perfectly shaped biphasic wave leaving a zero residual membrane potential. The model then further predicts that the increase in required effective current from this $I_o$ value is proportional to the excess membrane potential squared. In other words:

$$I_{eff} = I_o + kV_m^2 \tag{22}$$

Advantages of the New Model

Referring again to FIG. 4, one advantage of using the selectively configurable topology of capacitors 130, 132 for delivery of first phase 152 can be seen by examining curve 164. The cell membrane voltage as represented in curve 164 increase to about 0.35 at the end of the parallel configuration at point 155. At this point, the cell membrane voltage rapidly charges to a level in excess of 0.40 in less than about 3.0 ms. This same relative cell membrane voltage, when compared to delivery by a conventional biphasic countershock, would take at least 4.0 ms to achieve the same level. Consequently, the cell membrane voltage 162 is charged more rapidly and in a more optimal time by the conversion from parallel to series mode during delivery of a countershock in accordance with the present invention.

This advantage can be quantified by calculating the effective current of first phase 152 using Equation (19). The optimization here results from the desire to deliver as much charge from capacitors 130, 132 as possible (which for a fixed capacitance will necessarily require a longer duration d) without increasing the size of the denominator of Equation (19) excessively. In the case of the example shown in FIG. 4, capacitors 130, 132 each have an effective capacitance of 30 $\mu$F. In a parallel mode, this results in a total effective capacitance for the ICD of 60 $\mu$F, whereas in a series mode, the total effective capacitance for the ICD will be 15 $\mu$F. If a total energy for the device is limited to 17 J, then the maximum voltage would be 753 V. Using a duration of 1.95 ms for the "parallel" mode of first phase 152 and a duration of 0.8 ms for the "series" mode of first phase 152, the charge delivered in parallel mode is 21.6 mC and the charge delivered in series mode is 7.7 mC for a total overall charge for first phase 154 of 29.3 mC over a total duration of 2.75 ms, yielding an effective current ($I_e$) of 5.8 A (assuming a chronaxie duration of 2.7 ms).

Figure 5:
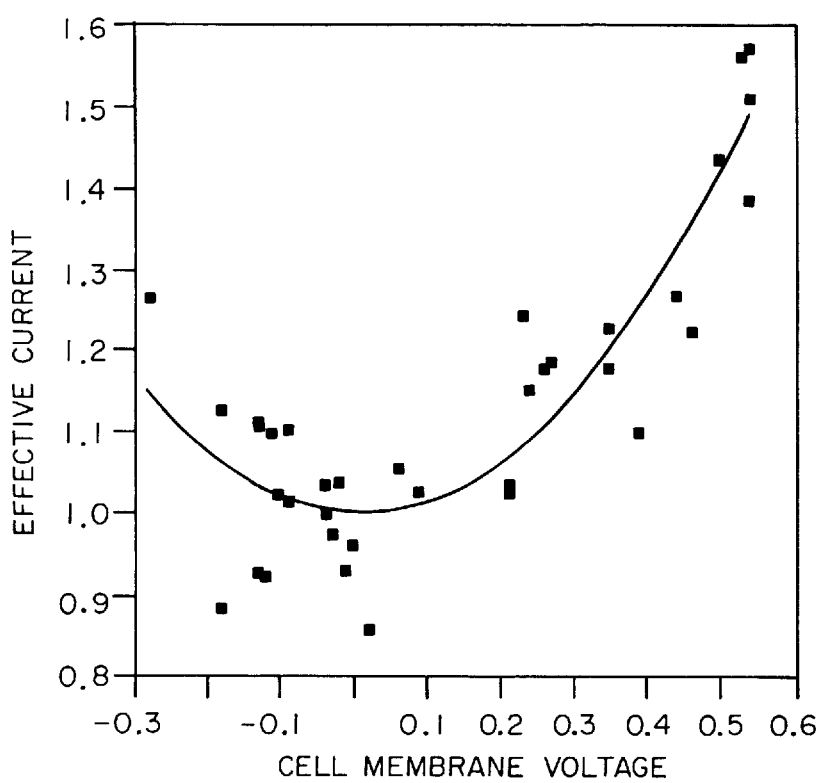
FIG. 5 is a graph depicting the advantage of the biphasic model described by the present invention.

Referring to FIG. 5, a graph of the residual membrane voltage versus effective current is shown for various theoretical and empirical studies of defibrillation effectiveness of biphasic waveforms. This graphs demonstrates that the lowest effective current required for successful defibrillation corresponds with a residual cell membrane voltage of 0 volts after the second phase of a biphasic waveform. For the reasons described above, when the residual cell membrane voltage is removed, the instances of subsequent conduction problems and refibrillation are decreased, thereby decreasing the need for a larger initial effective current in order to achieve effective defibrillation.

Application of the Model to Mode Reversal Energy Discharge Systems

Referring again to FIG. 4, it can be seen that in the embodiment having a series mode topology for capacitors 130, 132 in second phase 154, the electrical charge remaining in capacitors 130, 132 is completely depleted (shown at point 172), well prior to the discharge of cell membrane voltage 168 (shown at point 174). This is because, in a series mode topology, the time constant for the ICD having an effective resistance of 15 $\mu$F into a presumed 50 $\Omega$ interelectrode resistance will be only 0.75 ms. As a result, all of the remaining charge in capacitors 130, 132 is completely depleted at point 172 in less than about 2.5 ms. After point 172, cell membrane voltage 168 will continue to discharge, as shown, in part due to the Helmholz capacitance between the electrode leads. However, the discharge of cell membrane voltage 168 from the time corresponding to point 172 until the time corresponding to point 174 is non-optimal in terms of restoring cell membrane voltage 168 to a residual voltage of 0 volts as quickly as possible.

Figure 6:
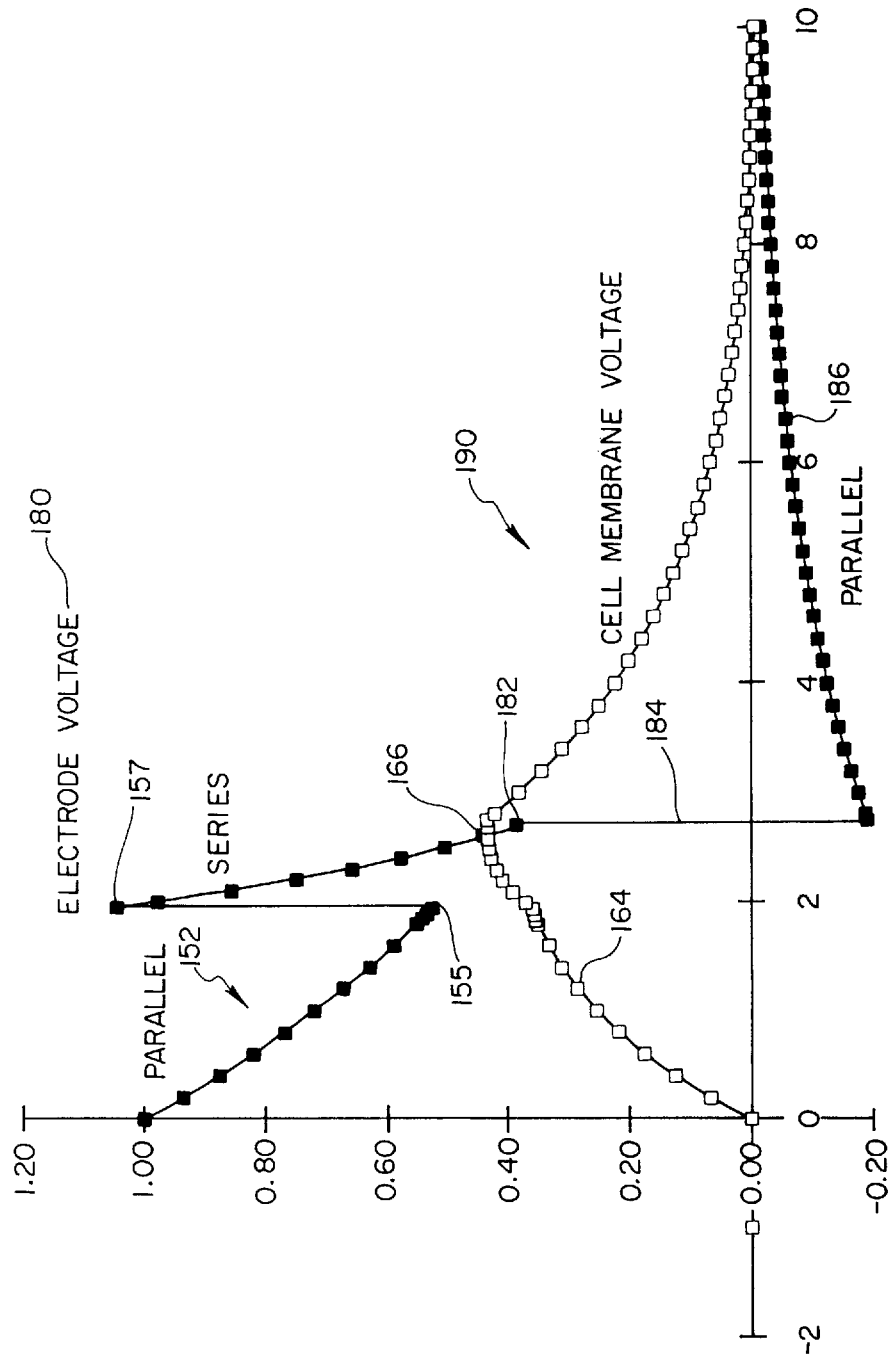
FIG. 6 depicts a representative voltage output for a mode reversal biphasic waveform as generated in accordance with the present invention.

The present invention improves upon the ideas disclosed in the parent applications to achieve a more optimal duration of the second phase of a biphasic waveform. As shown in FIG. 6, a first phase 152 of electrode voltage 180 is identical to first phase 152 for electrode voltage 150 as shown in FIG. 4. At point 182, however, the topology of capacitors 130, 132 is reverted back to a parallel configuration by controller 108 during transition 184 such that an electrode voltage for a second phase 186 has a longer effective duration. In this way, cell membrane voltage 190 during second phase 186 is more quickly decreased to zero volts. In the example shown, the difference in duration of second phase 154 versus second phase 186 is approximately 2 ms (10 ms for 154 vs. 8 ms for 186). The longer duration of second phase 186 is due to the fact that, by reverting to a parallel mode topology for second phase 186, the time constant for the ICD is effective increased by a factor of 4 from about 0.75 ms, to about 3.0 ms. The allows the remaining electrical energy stored in capacitors 130, 132 to be discharged more slowly, thereby actively pulling cell membrane voltage back to the desired zero residual voltage value for the entire duration of second phase 186.

It will be apparent that the advantages of the present invention are more apparent when capacitors 130, 132 have smaller effective capacitance values because these smaller effective capacitances directly relate to smaller time constants for the ICD. Because smaller capacitances are more effective in the delivery of optimal effective currents, the present invention is an important improvement for such optimized ICDs. If, for example, an ICD were constructed in accordance with the present invention, but having effective capacitance values of at least 120 $\mu$F, as is the case for all existing ICDs, the total effective capacitance of such an ICD configured in a series topology would be 60 $\mu$F, with a time constant of 3 ms—the same time constant which occurs for a parallel combination of the preferred embodiment of the present invention. Accordingly, while there would be less need for the present invention in this example, the advantage of having a faster return to zero residual volts at the end of the second phase is accomplished in either case.

It should also be noted that controller 108 can be configured to control the discharge of first phase 152 in response to a variety of preprogrammed criteria maintained by controller 108, including changing topology as a function of a fixed duration, a fixed tilt, minimum duration, minimum tilt, or any combination thereof, including a minimum of either a fixed duration or a fixed tilt. Similarly, controller 108 can also control second phase 154 so as to truncate this phase if necessary in the event that cell membrane voltage 180 returns to a zero residual voltage prior to the complete discharge of capacitors 130, 132 in the series topology configuration.

We claim:

1. An implantable cardioverter defibrillator apparatus for discharging a mode reversal biphasic electrical countershock to an ailing human heart through at least two implantable electrodes located proximate the heart, the apparatus comprising:

an internal power source for providing electrical energy;

a capacitance system, electrically connected between the power source and the electrodes, for storing electrical energy to generate a first phase and a second phase of the biphasic countershock, the capacitance system including at least two capacitor units each having separably switchable cathodes and anodes; and control means, operatively coupled to the power source and the capacitance system, for controlling delivery of the first phase and second phase of the biphasic countershock from the capacitance system to the electrodes in response to a sensing of a cardiac dysrhythmia such that the first phase has a first polarity across the electrodes and the at least two capacitor units are configured first in a parallel configuration and then in a series configuration during the first phase and the second phase has a second polarity across the electrodes and the at least two capacitor units are configured in a parallel configuration during at least a portion of the second phase.

2. The apparatus of claim 1 wherein there are two capacitor units, each of which is comprised of a pair of electrolytic capacitors electrically connected in series.

3. The apparatus of claim 1 wherein the control means controls a duration and a topology for the first and second phase in response to a preprogrammed criteria selected from the set comprising: a fixed duration, a fixed tilt, a minimum duration, a minimum tilt, or any combination thereof.

4. A method for operating an implantable cardioverter defibrillator device implanted within a human patient and electrically connected to at least two implantable electrodes located proximate a human heart to treat a cardiac arrhythmia by delivering a mode reversal biphasic electrical countershock, the method comprising the device-implemented steps of:

(a) sensing for a cardiac dysrhythmia in a human patient;

(b) in response to a sensing of a cardiac arrhythmia, performing the steps of:

(b1) charging a capacitive charge storage system to a high voltage charge value using a low voltage power source, the capacitive charge storage system including at least two capacitor units each having separably switchable cathodes and anodes;

(b2) discharging at least a first portion of the charge value stored in the capacitive charge storage system through the electrodes with the at least two capacitor units configured first in parallel and then in series to produce the first phase of the biphasic countershock;

(b3) discharging at least a second portion of the charge value stored in the capacitive charge storage system through the electrodes with the at least two capacitor units configured in parallel to produce the second phase of the biphasic countershock having an opposite polarity from the first phase.

5. The method of claim 4 wherein step (b2) is accomplished such that a duration and a topology for the first phase are selected in response to a preprogrammed criteria from the set comprising: a fixed duration, a fixed tilt, a minimum duration, a minimum tilt, or any combination thereof.

6. The method of claim 4 wherein step (b3) is accomplished such that a duration and a topology for the second phase are selected in response to a preprogrammed criteria from the set comprising: a fixed duration, a fixed tilt, a minimum duration, a minimum tilt, or any combination thereof.

7. The method of claim 4 wherein more than two capacitor units are utilized in step (b1).

* * * * *